United States Patent [19]

Parks et al.

[11] Patent Number: 4,560,558

[45] Date of Patent: Dec. 24, 1985

[54] 3-ALKYL-8-CHLORO-5,6-DIHYDROFURO-[3,2-f]-1,2-BENZISOXAZOLE-6-CARBOXYLIC ACIDS

[75] Inventors: James A. Parks, North Chicago; Jacob J. Plattner, Libertyville, both of Ill.

[73] Assignee: Abbott Laboratories, North Chicago, Ill.

[21] Appl. No.: 494,751

[22] Filed: May 16, 1983

[51] Int. Cl.[4] .................. C07D 261/20; A61K 31/42
[52] U.S. Cl. .................................... 514/379; 548/241
[58] Field of Search ................. 548/241, 242; 424/272

[56] References Cited

U.S. PATENT DOCUMENTS 3,631,174 12/1971 Remers et al. ..................... 548/242
3,891,664 6/1975 Suzuki et al. ...................... 548/241

FOREIGN PATENT DOCUMENTS 2754068 6/1978 Fed. Rep. of Germany ...... 424/285
155166 5/1982 German Democratic Rep. .................................... 548/241

5104273 8/1980 Japan .................................... 424/272

Primary Examiner—Donald G. Daus
Assistant Examiner—G. Hendricks
Attorney, Agent, or Firm—Steven F. Weinstock; Dennis K. Shelton

[57] ABSTRACT

Disclosed are compounds of the formula:

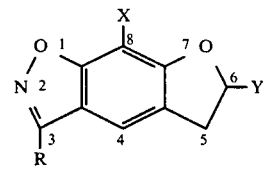

wherein X is hydrogen, loweralkyl, loweralkoxy or halo, Y is hydroxymethyl, carboxyl, carboxamido or carboloweralkoxy, and R is cyclohexyl, benzyl, norbornyl, loweralkyl, or a pharmaceutically acceptable salt thereof.

The compounds are effective as diuretic agents.

18 Claims, No Drawings

3-ALKYL-8-CHLORO-5,6-DIHYDROFURO-[3,2-f]-1,2-BENZISOXAZOLE-6-CARBOXYLIC ACIDS

BACKGROUND OF THE INVENTION

This invention relates to derivatives of the furo[3,2-f]-1,2-benzosoxazole ring system; specifically, compositions for the treatment of hypertension, cardiac failure, edema, and other conditions involving fluid or electrolyte Accumulation. A highly versatile synthetic process for the preparation of these substances is described, as well as a diuretic composition in dosage unit form.

Derivatives of the fully aromatic furobenzisoxazole system have been previously disclosed and have shown a variety of applications stemming from their biological activity. In the *Journal of the Indian Chemical Society,* Vol. 54, No. 9, pp. 875–877 (1977), and in the *Indian Journal of Chemistry,* Vol. 1513, No. 11, pp. 1058–1059 (1977), Thakar et al. describe some dialkyl derivatives with antifungal activity. Methyl derivatives in the 3-position were also reported by Hismat et al. in *Zeitschrift fur Naturforschung,* Vol. 336, pp. 1491–1495 (1978), as being obtained from the natural products visnaginone and khellinone. these syntheses, however, make no provision for variation of the substituents in the 6 and 8 positions and are relatively inflexible as regards the 3-substituent. They do not afford the substitution pattern herein described.

The object of this invention is to provide compositions of utility as diuretic agents, and to provide a general synthesis of these and other related compounds.

SUMMARY OF THE INVENTION

Described are compounds of the formula

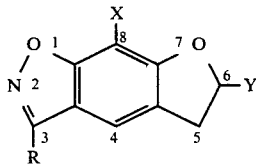

wherein X is hydrogen, loweralkyl, loweralkoxy or halo, Y is hydroxymethyl, carboxyl, carboxamido or carboloweralkoxy, and R is cyclohexyl, benzyl, norbornyl or a straight or branched chain alkyl group of from one to six carbon atoms, or a pharmaceutically acceptable salt thereof.

The terms "loweralkyl" and "loweralkoxy" as used herein refer to straight or branched chain alkyl radicals containing from 1 to 6 carbon atoms including but not limited to methyl, ethyl, n-propyl, iso-propyl, n-butyl, sec-butyl, t-butyl, 2-methylhexyl, n-pentyl, 1-methylbutyl, 2,2-dimethylbutyl, 2-methylpentyl, 2,2-dimethylpropyl, n-hexyl and the like.

The term "halo" as used herein refers to chloro, bromo, fluoro and iodo.

The term "pharmaceutically acceptable salts" includes nontoxic metallic salts such as the sodium, potassium, calcium magnesium or ammonium salt. These can be prepared by reacting the appropriate carboxylic acid with the appropriate hydroxide or carbonate.

The present compounds may be administered to warm-blooded animals orally or parenterally. They can generally be administered with a pharmaceutical carrier. The term "pharmaceutical carrier", for the purpose of the present invention, is intended to refer to any medium that is suitable for the preparation of a dosage unit form, and thus includes the tablet medium or a pharmaceutically acceptable vehicle or solvent such as is ordinarily used in the preparation of intravenous or intramuscular solutions. The compounds of this invention can be combined with other compounds having diuretic, antihypertensive or other cardiovascular activity.

A pharmaceutical composition containing the compound can be administered to warm-blooded animals in parenteral or oral dosage forms. For oral administration, amounts of from about 0.1 to 200 mg/kg per day per patient are useful, with the total dose of up to 1 gm. per day being a suitable range for large animals, including humans. A preferred dosage range is 50 to 1000 mg. total dosage daily in a single or divided dose. The whole dosage range described increases the total urinary excretion from about 2 to about 10-fold in most animals. From these figures, it is apparent that the new diuretic compounds are particularly effective in increasing urinary excretion in most animals.

For all dosage forms, the above exemplified compounds can be placed in capsules, formulated into pills, wafers or tablets in conventional fashion together with pharmaceutical carriers well known in the art. Tablets may be prepared for immediate release of the active compound or they may be made enteric, i.e., whereby the active ingredient is released slowly over a period of several hours from within the intestinal tract.

DETAILED DESCRIPTION OF THE INVENTION

In order to illustrate the manner in which the above compounds may be prepared and the properties of the compounds, reference is made to the following examples, which, however, are not meant to limit or restrict the scope of the invention in any respect.

The furo[3,2-f]-1,2-benzisoxazole derivatives of the invention can be prepared by the following method: A 2-substituted-6-methoxybenzofuran (or 6-methoxydihydrobenzofuran) derivative is acylated with an appropriate aroyl or alkanoyl halide or anhydride and a Lewis acid under Friedel-Crafts conditions. This substrate is preferably a 2-carboalkoxy or 2-(O-protected hydroxymethyl) compound, and the catalyst of choice is anhydrous aluminum chloride. The ortho-phenol functionality is then unmasked either separately or in situ by the use of additional Lewis acid and slightly more vigorous conditions.

The ester protecting group is removed by any of the methods known to the art; typically, aqueous or alcoholic base, aqueous acid or anhydrous Lewis acid may be used. An anti-oxime may then be selectively formed on the carbonyl at the 5-position by treatment with excess hydroxylamine hydrochloride, ideally in refluxing pyridine. Although formation of the oxime in the presence of an alkyl ester is feasible and has been carried out, the ease of hydrolysis and reesterification and the increase in overall yield amply justify the additional steps.

After replacement of the ester functionality under the usual conditions, the oxime may be acetylated or otherwise acylated. Treatment of such an adduct with anhydrous base in a polar, aprotic solvent (e.g., sodium or potassium hydride in N,N,-dimethylformamide) forms the ortho-phenoxide anion, which cyclizes to produce the desired tricyclic system in relatively high overall yield.

The 2-substituent may then be deprotected or elaborated according to the product sought, by conventional methods.

REPRESENATIVE SYNTHETIC SCHEME

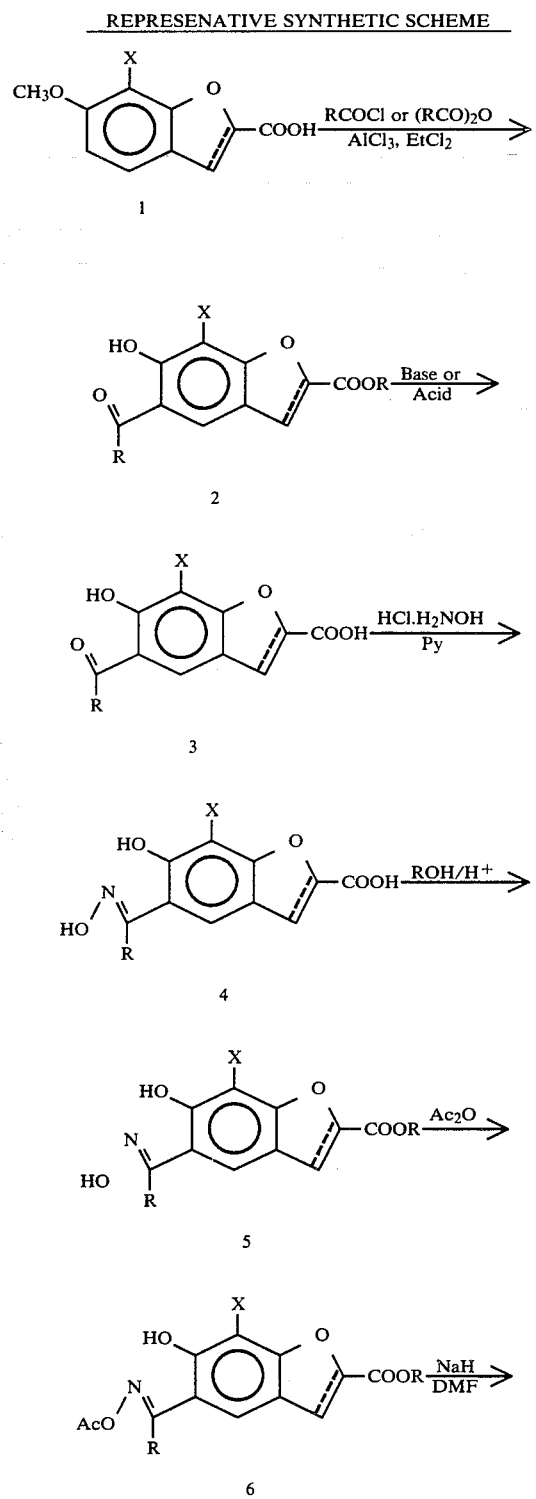

-continued
REPRESENATIVE SYNTHETIC SCHEME

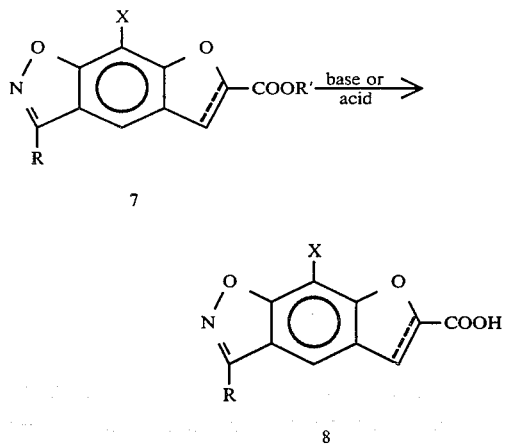

EXAMPLE 1

METHYL 5-ACETYL-7-CHLORO-2,3-DIHYDRO-6-HYDROXYBENZOFURAN-2-CARBOXYLATE (2a)

To 1,2-dichloroethane (50 ml) were added sequentially methyl 7-chloro-2,3-dihydro-6-methoxybenzofuran-2-carboxylate-(1a) (4.53 g, 0.0187 mol) and acetic anhydride (3.5 ml, 0.0373 mol). The solution was stirred in an ice/brine bath at 0°–5° C. and treated with anhydrous aluminum chloride (9.95 g, 0.0747 mol) portionwise over 20 minutes. Cooling was removed after 1.5 hours and the was mixture left to stir at room temperature overnight.

The reaction mixture was decanted into iced dilute hydrochloric acid, producing a precipitate which was extracted into ethyl acetate, washed with brine, dried over anhydrous magnesium sulfate, and evaporated. The crystalline product was triturated in chloroform/hexane and recrystallized from acetonitrile with water to yield 81.9% of light pink crystals, m.p. 175°–177° C. Anal. ($C_{12}H_{11}ClO_5$) C,H.

EXAMPLE 2

ETHYL 7-CHLORO-2,3-DIHYDRO-6-HYDROXY-5-PROPIONYLBENZOFURAN-2-CARBOXYLATE (2b)

To 1,2-dichloroethane (50 ml) were added ethyl 7-chloro-2,3-dihydro-6-methoxybenzofuran-2-carboxylate (1b) (4.25 g, 0.01656 mol) and propionyl chloride (2.58 ml, 0.03311 mol). The solution was stirred on an ice bath and treated with anhydrous aluminum chloride (6.62 g, 0.04967 mol) at 0°–5° C. for 45 minutes. An additional portion of aluminum chloride (2.21 g, 0.01656 mol) was added and the mixture left to stir overnight.

The reaction was worked up as per Example 1 to yield 80.9% of white crystals, m.p. 109°–111° C., after recrystallization from ethyl acetate/hexane. Anal. ($C_{14}H_{15}ClO_5$) C,H.

EXAMPLE 3

ETHYL 7-CHLORO-2,3-DIHYDRO-6-HYDROXY-5-ISOVALEROYL BENZOFURAN-2-CARBOXYLATE (2c)

Ethyl 7-chloro-2,3-dihydro-6-methoxybenzofuran-2-carboxylate and isovaleric anhydride were reacted under identical conditions to the above. After 24 hours, incomplete removal of the methoxy group (as evidenced by thin-layer chromatography) demanded an additional treatment with 1 eq of aluminum chloride.

The mixture was stirred for six hours and worked up as in Example 1 to yield a white crystalline solid, m.p. 84°–85° C. (32.5%). Anal. ($C_{16}H_{19}ClO_5$) C,H.

EXAMPLE 4

ETHYL 7-CHLORO-5-(O-FLUOROBENZOYL)-6-HYDROXYBENZOFURAN-2-carboxylate (2d)

Ethyl 7-chloro-6-methoxybenzofuran-2-carboxylate (12.68 g, 0.05 mol) and O-flurobenzoyl chloride (11.9 ml, 0.1 mol) were dissolved in 1,2-dichloroethane (100 ml) and treated with anhydrous aluminum chloride (26.66 g, 0.2 mol) in small portions over 30 minutes. The mixture was then heated overnight at reflux. Work-up as in Example 1 resulted in an oil which was chromatographed on silica with benzene yielding 38.3% of off-white crystals, m.p. 132°–134° C., after recrystallization from tetrahydrofuran/hexane and ethanol/water.

Anal. ($C_{18}H_{12}ClFO_5$) C,H.

EXAMPLE 5

ETHYL 7-CHLORO-2,3-DIHYDRO-5-(O-FLUROBENZOYL)-6-HYDROXYBENZOFURAN-2-CARBOXYLATE (2e)

A solution of ethyl 7-chloro-2,3-dihydro-6-methoxybenzofuran-2-carboxylate (7.79 g, 0.0304 mol) and O-flurobenzoyl chloride (7.25 ml, 0.0607 mol) in 80 ml of 1,2-dichloroethane was stirred on an ice/brine bath and treated with aluminum chloride (12.13 g, 0.0911 mol) in small portions, keeping the temperature below 5° C. After 45 minutes, cooling was removed and the reaction mixture was allowed to stir at room temperature for three hours. Decantation into iced dilute aqueous hydrochloric acid and gentle warming produced a pale yellow oil which was extracted into ethyl acetate. The extract was washed with brine, dried over anhydrous magnesium sulfate, decolorized with charcoal and evaporated, yielding 69.2% of 2e, m.p. 119°–119.5° C., after recrystallization from ethyl acetate/n-hexane. Anal. ($C_{18}H_{14}ClFO_5$) C,H.

EXAMPLE 6

ETHYL 2,3-DIHYDRO-5-(O-FLUOROBENZOYL)-6-METHOXY-7-METHYLBENZOFURAN-2-CARBOXYLATE

A solution ethyl of 2,3-dihydro-6-methoxy-7-methylbenzofuran-2-carboxylate (2.7 g, 0.011 mol) in 1,2-dichloroethane (30 ml) was stirred at 0°–5° C. and treated with anhydrous aluminum chloride (4.57 g, 0.003 mole) in small portions. After 10 minutes the reaction mixture was poured onto ice and extracted into methylene chloride. The organic layer was washed with brine, dried over magnesium sulfate, and evaporated. The residue was chromatographed on silica with methylene chloride to yield 68.0% of the methyl ether, m.p., 101.5°–102.5° C. Anal. ($C_{20}H_{19}FO_5$) C,H.

EXAMPLE 7

ETHYL 2,3-DIHYDRO-5-(O-FLUOROBENZOYL)-6-HYDROXY-7-METHYLBENZOFURAN-2-CARBOXYLATE (2f)

A solution of the foregoing product (2.0 g, 0.0056 mol) in methylene chloride (20 ml) was stirred at 0° C. and treated by dropwise addition with boron triboromide (6.14 ml of 1.0M methylene chloride solution). After 15 minutes, the reaction was poured into ice water and extracted with methylene chloride. The organic layer was dried over magnesium sulfate and evaporated to afford 93.0% of 2f (63.2% over two steps) after recrystallization from ethanol, m.p. 103°–105° C. Anal. ($C_{19}H_{17}FO_5$) C,H.

EXAMPLE 8

5-ACETYL-7-CHLORO-2,3-DIHYDRO-6-HYDROBENZOFURAN-2-CARBOXYLIC ACID (3a)

The acetyl adduct from Example 1 (3.96 g, 0.00146 mol) was suspended in distilled water (50 ml) and treated with 2M aqueous sodium hydroxide (9.2 ml, 1.25 eq) at room temperature for 2 hours. Acidification with concentrated hydrochloric acid produced a fine white crystalline precipitate which was collected by filtration and dried in vacuo giving 94.0% of the acid, m.p. 227°–231° C. Anal. ($C_{11}H_9ClO_5$) C,H. Mol. wt. (HRMS) Calc'd: 256.0138; Found: 256.0138.

EXAMPLE 9

7-CHLORO-2,3-DIHYDRO-6-HYDROXY-5-PROPIONYLBENZOFURAN-2-CARBOXYLIC ACID (3b)

The title compound was prepared in quantitative yield from the compound 2b by the method of Example 8 giving white crystals, m.p. 227°–229° C. Anal. ($C_{12}H_{11}ClO_5$) C,H. Mol. Wt. (HRMS) Calcd: 270.0295; Found: 270.0293.

EXAMPLE 10

7-CHLORO-2,3-DIHYDRO-6-HYDROXY-5-ISOVALEROYLBENZOFURAN-2-CARBOXYLIC ACID (3c)

The above was obtained in like fashion from 2c, producing 93.2% of white crystals, m.p. 174°–176° C. Mol. wt. (HRMS) Calc'd: 298.0608; Found: 298.0599.

EXAMPLE 11

7-CHLORO-2,3-DIHYDRO-5-(O-FLUOROBENZOYL-6-HYDROXYBENZOFURAN-2-CARBOXYLATE (3e)

A solution of 2e (6.69%, 0.01834 mol) in 100 ml of methylene chloride was cooled on an acetonitrile/dry ice bath, treated dropwise with 55 ml of 1M boron tribromide/methylene chloride solution, and stirred at room temperature overnight. The resulting orange mixture was decanted into dilute iced aqueous hydrochloric acid and warmed gently to room temperature, stirred for 2 hours, and extracted into ethyl acetate. The organic phase was washed with brine, dried over anhydrous magnesium sulfate, and decolorized with charcoal. Evaporation and recrystallization from ethyl acetate/n-hexane gave the free acid in 53.8% yield, m.p. 209.5°–212.5° C. Anal. ($C_{16}H_{11}ClFNO_5$) C,H.

EXAMPLE 12

(E)-5-ACETYL-7-CHLORO-2,3-DIHYDRO-6-HYDROXYBENZOFURAN-2-CARBOXYLIC ACID OXIME (4a)

A mixture of the acid 3a from Example 8 (2.95 g, 0.0115 mol) and hydroxylamine hydrochloride (5.55 g, 0.0804 mol) was added to pyridine (100 ml) and heated at reflux for 7 hours. The pyridine was then removed on a rotary evaporator and chased with ethanol. The residue was dissolved in ethyl acetate, washed with dilute aqueous hydrochloric acid and brine solutions, dried over anhydrous magnesium sulfate, and evaporated to dryness, giving 99.5% of white crystals, m.p. 234°–235° C. Anal. ($C_{11}H_{10}ClNO_5$) C,H,N. (HRMS) Calc'd: 271.0247; Found: 271.0246.

EXAMPLE 13

(E)-7-CHLORO-2,3-DIHYDRO-6-HYDROXY-5-PROPIONYLBENZOFURAN-2-CARBOXYLIC ACID OXIME (4b)

The acid 3b was processed analogously to the above, affording 96.1% of white crystals after trituration overnight in hexane, m.p. 198°–201° C.(d). Anal. ($C_{12}H_{12}ClNO_5$) C,H,N.

EXAMPLE 14

(E)-7-CHLORO-2,3-DIHYDRO-6-HYDROXY-5-ISOVALEROYLBENZOFURAN-2-CARBOXYLIC ACID OXIME (4c)

Treatment of acid 3c as above resulted in a yield of 88.9% of 4c. Mol. Wt. (HRMS) Calc'd: 313.0717; Found: 313.0716.

EXAMPLE 15

(E)-7-CHLORO-2,3-DIHYDRO-5-(O-FLUROBENZOYL-6-HYDROXYBENZOFURAN-2-CARBOXYLIC ACID OXIME (4e)

The acid 3e was made into the oxime in a manner identical to the above, in quantitative yield. An analytical sample, m.p. 195°–197° C., was obtained by recrystallizing twice from ethyl acetate/hexane. Anal. ($C_{16}H_{11}ClFNO_5$) C,H,N.

EXAMPLE 16

ETHYL (E)-5-ACETYL-7-CHLORO-2,3-DIHYDRO-6-HYDROXYBENZOFURAN-2-CARBOXYLATE OXIME (5A)

The acid 4a was esterified by stirring in a solution of tetrahydrofuran, ethanol, and concentrated sulfuric acid (39:60:1) for 16 hours at room temperature. The resulting solution was evaporated and the residue dissolved in ethyl acetate, washed with aqueous sodium bicarbonate and brine, dried over magnesium sulfate, and evaporated. Recrystallization from ethyl acetate/hexane furnished 76.1% of white crystals, m.p. 154°–155° C. Anal. ($C_{13}H_{14}ClNO_5$) C,H,N.

EXAMPLE 17

ETHYL (E)-7-CHLORO-2,3-DIHYDRO-6-HYDROXY-5-PROPIONYLBENZOFURAN-2-CARBOXYLATE OXIME (5b)

The above was prepared analogously from 4b in 87.2% yield, m.p. 145.5°–147° C. Anal. ($C_{14}H_{16}ClNO_5$) C,H,N.

EXAMPLE 18

ETHYL (E)-7-CHLORO-2,3-DIHYDRO-6-HYDROXY-5-ISOVALEROYLBENZOFURAN-2-CARBOXYLATE OXIME (5e)

The above in like fashion was produced from 4e in 75.4% yield, m.p. 159°–162° C. Anal. ($C_{16}H_{20}ClNO_5$) C,H,N.

EXAMPLE 19

ETHYL (E)-7-CHLORO-2-3-DIHYDRO-5-(O-FLUOROBENZOYL)-6-HYDROXYBENZOFURAN-2-CARBOXYLIC ACID OXIME (5e)

The above resulted from esterification of 4e in absolute ethanol with a catalytic quantity of sulfuric acid, and work-up as previously described, in 74% yield, m.p. 171°–172° C. Anal. ($C_{18}H_{15}ClFNO_5$) C,H,N.

EXAMPLE 20

ETHYL (E)-2,3-DIHYDRO-5-(O-FLUOROBENZOYL)-6-HYDROXY-7-METHYLBENZOFURAN-2-CARBOXYLATE OXIME (5f)

The above was obtained directly from 2f without hydrolysis/reesterification, as follows: A mixture of 2f (1.6 g, 0.00465 mol) and hydroxylamine hydrochloride (1.55 g, 0.0223 mol) was heated at reflux in pyridine (7 ml) for 4 hours. The solvent was evaporated and the residue was partitioned between ethyl acetate and 5% aqueous hydrochloric acid. From the organic phase was obtained a crystalline product, m.p. 70°–71° C., in 20% yield after chromatographic purification on silica. Anal. ($C_{19}H_{18}FNO_5$) C,H,N.

EXAMPLE 21

ETHYL (E)-5-ACETYL-7-CHLORO-2,3-DIHYDRO-6-HYDROXYBENZOFURAN-2-CARBOXYLATE-O-ACETYLOXIME (6a)

Oxime 5a (2.88 g, 0.001 mol) was dissolved in warm acetic anhydride (50 ml) and left to stir overnight. The precipitate was collected by filtration and recrystallized from absolute ethanol to yield 64.7% of white crystals, m.p. 154°–157° C. Anal. ($C_{15}H_{16}ClNO_6$) C,H,N,Cl. Mol. wt. (HRMS) Calc'd: 341.0666; Found: 341.0661.

EXAMPLE 22

ETHYL (E)-7-CHLORO-2,3-DIHYDRO-6-HYDROXY-5-PROPIONYL-BENZOFURAN-2-CARBOXYLATE-O-ACETYLOXIME (6b)

5b (3.45 g, 0.011 mol) was stirred in acetic anhydride overnight. Evaporation ad trituration in ethanol gave 89.2% of white crystals, M.P. 140°–142° C. Anal. ($C_{16}H_{18}ClNO_6$) C,H,N.

EXAMPLE 23

ETHYL (E)-7-CHLORO-2,3-DIHYDRO-6-HYDROXY-5-ISOVALEROYL-BENZOFURAN-2-CARBOXYLATE-O-ACETYLOXIME (6c)

The above was made by treatment of oxime 5c as above in 77.0% yield, m.p. 114°–115° C. after trituration in ethyl acetate/ethanol. Anal. ($C_{18}H_{22}ClNO_6$) C,H,N.

EXAMPLE 24

ETHYL 8-CHLORO-5,6-DIHYDRO-3-METHYLFURO[3,2-f]-1,2-BENZISOXAZOLE-6-CARBOXYLATE (7a)

The acetate 6a (2.03 g, 0.00594 mol) was taken up in dry dimethylformamide (15 ml), stirred on an ice bath under inert atmosphere, and treated with sodium hydride/mineral oil 50% dispersion (300 mg, 1.05 eq). Cooling was removed and stirring continued for 4 hours, after which the mixture was decanted into chilled brine and extracted with ethyl acetate. The combined extracts were washed copiously with brine, dried over anhydrous magnesium sulfate, decolorized with charcoal, and evaporated to dryness. Recrystallization from ethyl acetate/hexane furnished 7a in 76.3% yield, m.p. 123°–124° C. Anal. ($C_{13}H_{12}ClNO_4$) C,H,N.

EXAMPLE 25

ETHYL 8-CHLORO-5,6-DIHYDRO-3-ETHYLFURO[3,2-f]-1,2-BENZISOXAZOLE-6-CARBOXYLATE (7b)

Compound 6b was cyclized using an identical procedure. White crystals, m.p. 95°–96° C., were obtained in 77.8% yield on recrystallization from chloroform/hexane. Anal. ($C_{14}H_{14}ClNO_4$) C,H,N.

EXAMPLE 26

ETHYL 8-CHLORO-5,6-DIHYDRO-3-(2-METHYLPROPYL)FURO[3,2-f]-1,2-BENZISOXAZOLE-6-CARBOXYLATE (7c)

The above was made analogously in 59.3% yield, m.p. 74°–75° C., after recrystallization from n-hexane at low temperature. Anal. ($C_{16}H_{18}ClNO_4$) C,H,N.

EXAMPLE 27

8-CHLORO-5,6-DIHYDRO-3-METHYLFURO[3,2-f]-1,2-BENZISOXAZOLE-6-CARBOXYLATE ACID (8a)

The ethyl ester was dissolved in a minimal amount of absolute ethanol and hydrolyzed with excess 2M aqueous sodium hydroxide solution. The insoluble sodium salt was collected by filtration an shaken with ethyl acetate/dilute aqueous hydrochloric acid. The organic phase was washed with brine, dried over anhydrous magnesium sulfate, and evaporated. Recrystallization of the residue from ethyl acetate/hexane gave a near-quantitative yield of the acid, m.p. 260°–263° C. Anal. ($C_{11}H_8ClNO_4$) C,H,N.

EXAMPLE 28

8-CHLORO-5,6-DIHYDRO-3-ETHYLFURO[3,2-f]-1,2-BENZISOXAZOLE-6-CARBOXYLIC ACID (8b)

Ester 7b was dissolved in minimal absolute ethanol and treated with excess alcohol potassium hydroxide at room temperature for 20 minutes, then diluted with water. Work-up as in the previous example and recrystallization from tetrahydrofuran/hexane gave white crystals, m.p. 213°–215° C., in 74.8% yield. Anal. ($C_{12}H_{10}ClNO_4$) C,H,N,Cl.

EXAMPLE 29

8-CHLORO-5,6-DIHYDRO-3-(2-METHYLPROPYL)FURO[3,2-f]-1,2-BENZISOXAZOLE-6-CARBOXYLIC ACID (8c)

The above was obtained by analogous treatment of 7c and recrystallization from ethyl acetate/hexane; m.p. 181°–183° C. Anal. ($C_{14}H_{14}ClNO_4$) C,H,N,Cl.

Compounds 3d, 5e, and 5f were also processed by this route and appropriate final products were obtained. All intermediates were examined by 60 MHz or 90 MHz proton NMR and found to possess observed spectral properties consistent with their proposed structures.

Diuretic screening of the compounds of this invention was conducted in normotensive rats using the following procedure.

Female rats (Sprague-Dawley), weighing 175–225 grams, are placed on a diet of sucrose and water overnight. DOCA (deoxycorticosterone acetate), is prepared as a 2.5% suspension in 0.2% hydroxypropyl methyl cellulose. Each rat is administered 0.2 ml subcutaneously of the DOCA suspension two hours prior to treatment with the test compound.

The suspension or solutions of test compounds are prepared daily. The compounds are suspended in 0.2% hydroxypropyl methylcellulose (vehicle) and administered orally (by gavage) in 2 ml/kg of the rat's body weight. Immediately after dosing, each rat is loaded with an isotonic mixture of NaCl and KCl in the ratio of 40:60 equivalent to 3% of the rat's body weight.

The rats are placed in individual stainless steel metabolism cages. No food or water is allowed during the experiment. Urine is collected for a four hour period. The volume of urine is measured at four hours and an aliquot is taken for analysis of urine sodium and potassium concentrations. Sodium and potassium are measured using an Instrumentation Labs Digital Flame Photometer. The data are reported in: volume - ml; sodium and potassium - meq/l.

Standard screening procedures involving the testing of two doses of each compound using 2 rats per dose in a 2-stage screening system. The normal screening doses are 30 and 100 mg/kg orally. Urinary excretion of sodium is expressed as meq/kg of the rat's body weight. The natriuretic potency of the compounds is reported as an $ED_2$. This is the oral dose (mg/kg) necessary to produce an excretion in the 0–4 hour period before dosing, of 2-milliequivalents of $Na^+$ per kilogram (meq/kg) in the rat urine.

When tested according to the above described procedure, the compound 8-chloro-5,6-dihydro-3-methylfuro[3,2-f]-1,2-benzisoxazole-6-carboxylic acid (Example 27) was found to have an $ED_2$ of 40 milligrams per kilogram.

The compounds of this invention can be combined with other cardiovascular drugs of different but complementary mechanisms, thereby providing, for example, additive diuretic and antihypertensive effects. Other compounds including the thiazide diuretics, potassium sparing diuretics such as triamterene or spironolactone, antihypertensive compounds including β-blockers such as propranolol, nadolol, atenolol or metoprolol, methyldopa, clonidine or reserpine, vasocialators such as hydralazine or prazosin can be added.

The preferred dosage range for the compounds of this invention is 20 to 100 mg total dosage daily in a single or divided dose. While the choice of and the amount of the agent to be combined with the compounds of this invention depends on the presence of contraindications and side effects as well as efficacy, suggested amounts of the compounds to be added are as follows: propanolol - 80 to 240 mg per day in divided doses; methyldopa - 500 to 1,000 mg daily in divided doses; reserpine - 1.0 mg daily in divided doses; Hydralizine - 50 to 300 mg daily in divided doses; and prazosin - 4 to 40 mg daily in divided doses.

While these amounts are preferably added to the preferred dosage range of the compounds of this invention, the choice of agent and the response to therapy may require use of a broader dosage range of the disclosed compounds, namely up to one gram per day in a single or divided dose.

What is claimed is:

1. A compound of the formula:

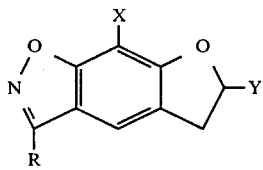

wherein X is hydrogen, loweralkyl, loweralkoxy or halo, Y is carboxyl, carboxamido or carboloweralkoxy, and R is cyclohexyl, or loweralkyl, or a pharmaceutically acceptable salt thereof.

2. A compound of claim 1 wherein X is loweralkyl or halo, Y is carboxy, and R is loweralkyl.

3. A compound of claim 1 wherein X is chloro, Y is carboxy, and R is methyl, ethyl or 2-methylpropyl.

4. A compound of claim 3 wherein R is methyl.

5. A compound of claim 3 wherein R is ethyl.

6. A compound of claim 3 wherein R is 2-methylpropyl.

7. A pharmaceutical composition useful as a diuretic which comprises a therapeutically effective amount of a compound of the formula:

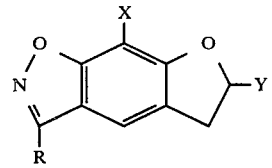

wherein X is hydrogen, loweralkyl, loweralkoxy or halo, Y is carboxyl, carboxamido or carboloweralkoxy, and R is cyclohexyl, or loweralkyl, or a pharmaceutically acceptable salt thereof, together with a pharmaceutically acceptable carrier.

8. A composition of claim 1 wherein X is loweralkyl or halo, Y is carboxy, and R is loweralkyl.

9. A composition of claim 1 wherein X is chloro, Y is carboxy, and R is methyl, ethyl or 2-methylpropyl.

10. A composition of claim 3 wherein R is methyl.

11. A composition of claim 3 wherein R is ethyl.

12. A composition of claim 3 wherein R is 2-methylpropyl.

13. A method of increasing diuresis in a patient comprising administering to a patient in need of such treatment a therapeutically effective amount of a diuretic agent of the formula:

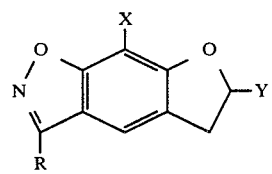

wherein X is hydrogen, loweralkyl, loweralkoxy or halo, Y is carboxyl, carboxamido or carboloweralkoxy, and R is cyclohexyl, or loweralkyl, or a pharmaceutically acceptable salt thereof.

14. A method of claim 1 wherein X is loweralkyl or halo, Y is carboxy, and R is loweralkyl.

15. A method of claim 1 wherein X is chloro, Y is carboxy, and R is methyl, ethyl or 2-methylpropyl.

16. A method of claim 3 wherein R is methyl.

17. A method of claim 3 wherein R is ethyl.

18. A method of claim 3 wherein R is 2-methylpropyl.

* * * * *